United States Patent
Komiya et al.

(10) Patent No.: US 10,036,077 B2
(45) Date of Patent: Jul. 31, 2018

(54) COVERED SEQUENCE CONVERSION DNA AND DETECTION METHODS

(71) Applicants: ABBOTT JAPAN CO., LTD., Chiba (JP); TOKYO INSTITUTE OF TECHNOLOGY, Tokyo (JP)

(72) Inventors: Ken Komiya, Tokyo (JP); Makoto Komori, Matsudo (JP); Toru Yoshimura, Matsudo (JP)

(73) Assignees: Abbott Laboratories, Abbott Park, IL (US); Tokyo Institute of Technology, Tokyo (JP)

( * ) Notice: Subject to any disclaimer, the term of this patent is extended or adjusted under 35 U.S.C. 154(b) by 216 days.

(21) Appl. No.: 14/597,981

(22) Filed: Jan. 15, 2015

(65) Prior Publication Data

US 2015/0197823 A1 Jul. 16, 2015

Related U.S. Application Data

(60) Provisional application No. 61/927,710, filed on Jan. 15, 2014.

(51) Int. Cl.
 *C12Q 1/68* (2018.01)
 *C12P 19/34* (2006.01)
 (Continued)

(52) U.S. Cl.
 CPC ............ *C12Q 1/707* (2013.01); *C12Q 1/682* (2013.01); *C12Q 1/689* (2013.01); *C12Q 1/6844* (2013.01);
 (Continued)

(58) Field of Classification Search
 None
 See application file for complete search history.

(56) References Cited

U.S. PATENT DOCUMENTS

| 4,683,195 A | 7/1987 | Mullis et al. |
| 4,683,202 A | 7/1987 | Mullis |

(Continued)

FOREIGN PATENT DOCUMENTS

| CN | 103789435 | 5/2014 |
| EP | 1 500 710 | 1/2005 |

(Continued)

OTHER PUBLICATIONS

International Search Report and Written Opinion of PCT Patent Application No. PCT/IB2015/000726 dated Sep. 10, 2015.
(Continued)

*Primary Examiner* — Young J Kim
(74) *Attorney, Agent, or Firm* — Audrey L. Bartnicki, Abbott Laboratories

(57) ABSTRACT

Disclosed are methods for detecting a target nucleic acid in sample, which include contacting the sample with an oligonucleotide having a hairpin structure, where the oligonucleotide includes, in the 5' to 3' direction, an arbitrary sequence, an endonuclease recognition site for a nicking reaction, a sequence complementary to the arbitrary sequence, and a sequence complementary to the target nucleic acid; a polymerase; and an endonuclease capable of nicking the endonuclease recognition site. The disclosure also provides compositions and kits comprising an oligonucleotide having a hairpin structure, where the oligonucleotide includes, in the 5' to 3' direction an arbitrary sequence, an endonuclease recognition site for a nicking reaction, a sequence complementary to the arbitrary sequence, and a sequence complementary to a target nucleic acid.

10 Claims, 9 Drawing Sheets

(51) Int. Cl.
| | |
|---|---|
| C12Q 1/70 | (2006.01) |
| C12Q 1/689 | (2018.01) |
| C12Q 1/6844 | (2018.01) |
| C12Q 1/682 | (2018.01) |

(52) U.S. Cl.
CPC ............ *C12Q 1/703* (2013.01); *C12Q 1/706* (2013.01); *C12Q 2600/158* (2013.01); *C12Q 2600/178* (2013.01)

(56) References Cited

U.S. PATENT DOCUMENTS

| | | | |
|---|---|---|---|
| 4,800,159 A | 1/1989 | Mullis et al. | |
| 5,958,700 A | 9/1999 | Nadeau et al. | |
| 6,316,200 B1 * | 11/2001 | Nadeau ................ | C12Q 1/6818 435/6.12 |
| 9,845,495 B2 | 12/2017 | Komiya | |
| 2003/0082590 A1 | 5/2003 | Van Ness et al. | |
| 2003/0165911 A1 | 9/2003 | Van Ness et al. | |
| 2004/0259102 A1 | 12/2004 | Kool | |
| 2005/0059005 A1 * | 3/2005 | Tuschl ................ | C12N 15/113 435/6.14 |
| 2008/0311564 A1 * | 12/2008 | Fort ...................... | C12Q 1/705 435/5 |
| 2009/0017453 A1 | 1/2009 | Maples et al. | |
| 2009/0081670 A1 | 3/2009 | Maples et al. | |
| 2010/1298220 | 5/2010 | Amara | |
| 2014/0017692 A1 | 1/2014 | Komiya | |
| 2016/0102339 A1 | 4/2016 | Komiya et al. | |
| 2016/0102345 A1 | 4/2016 | Komiya et al. | |

FOREIGN PATENT DOCUMENTS

| | | |
|---|---|---|
| JP | H07-114718 | 5/1995 |
| JP | H07-114718 B | 12/1995 |
| JP | 2005-516610 | 6/2005 |
| WO | 2000/28082 | 5/2000 |
| WO | 2002/16639 | 2/2002 |
| WO | 2003/066802 | 8/2003 |
| WO | 2003/066802 A3 | 8/2003 |
| WO | 2004-067726 | 8/2004 |
| WO | 2004/067764 | 8/2004 |
| WO | 2004/067765 | 8/2004 |
| WO | 2008/001376 | 1/2008 |
| WO | 2009/012246 | 1/2009 |
| WO | 2012/077819 | 6/2012 |
| WO | 2015114469 | 8/2015 |
| WO | 2016059473 | 4/2016 |
| WO | 2016059474 | 4/2016 |

OTHER PUBLICATIONS

Gill, et al. "Nucleic Acid Isothermal Amplification Technologies—A Review", Nucleosides, Nucleotides and Nucleic Acids, Taylor & Francis, US, vol. 27, No. 3, Mar. 1, 2008, pp. 224-243.
Tan, E. et al., "Isothermal DNA Amplification with Gold Nanosphere-Based Visual Colorimetric Readout for Herpes Simplex Virus Detection", Clinical Chemistry, 53, No. 11, pp. 2017-2020 (2007).
Tan, E. et al "Isothermal DNA Amplification Coupled with DNA Nanosphere-Based Colorimetric Detection", Analytical Chemistry, vol. 77, No. 24, pp. 7984-7992 (Dec. 15, 2005).
Tan, E. et al., "Specific versus Nonspecific Isothermal DNA Amplification through Thermophilic Polymerase and Nicking Enzyme Activities", Biochemistry, vol. 47, No. 38, pp. 9987-9999 (2008).
G.T. Walker, M.C. Little, J.G. Nadeau and D.D. Shank, Proc. Natl. Acad. Sci. USA, 89, 392-396 (1992).
Y. Weizmann, M.K. Beissenhirtz, Z. Cheglakov, R. Nowarski and I. Willner, Angew. Chem. Int. Ed., 45, 7384-7388 (2006).
International Preliminary Report, PCT/JP2011/078717, International Filing Date Dec. 12, 2011 (Tokyo Institute of Technology).
J. Van Ness, L.K. Ness and D.J. Galas, Proc. Natl. Acad. Sci. USA, 100 (8): 4504-4509 (Apr. 15, 2003).
Dirks, Robert M., Pierce, Niles A., PNAS, Oct. 26, 2004, vol. 101, No. 43, 15275-15278.
Huang, Jin, Wu, Yanrong, Chen, Yan, Zhu, Zhi, Yang, Xiaohai, Yang, Chaoyong, James, Wang, Kemin, Tan, Weihong, Angew, Chem. Int. Ed. 2011, 50, 401-404.
Niu, Shuyan, Jiang, Yu, Zhang, Susheng, Chem, Commun, 2010, 46, 3089-3091 (2010).
International Search Report, PCT/JP2011/078717, International Filing Date Dec. 12, 2011 (Tokyo Institute of Technology).
PCT International Search Report and Written Opinion dated Mar. 29, 2016 for PCT Patent Application No. PCT/IB2015/002145.
Veedu et al., "Locked Nucleic Acids: Promising Nucleic Acid Analogs for Therapeutic Applications," Chemistry & Biodiversity, vol. 7, 2010, 7 pages.
Yang et al., "Synthesis and investigation of deoxyribonucleic acid/locked nucleic acid chimeric molecular beacons," Nucleic Acids Research, vol. 35, 2007, 9 pages.
Vester et al., "LNA (Locked Nucleic Acid): High-Affinity Targeting of Complementary RNA and DNA," Biochemistry, vol. 43, 2004, 12 pages.
PCT, Notification of Transmittal of the International Search Report and the Written Opinion of the International Searching Authority, or the Declaration, in International Application No. PCT/IB2015/059986, dated Jun. 3, 2016 (16 pages).
Haiyun Liu et al., "High Specific and Ultrasensitive Isothermal Detection of MicroRNA by Paddlock Prob-Based Exponential Rolling Circle Amplification", Analytical Chemistry, vol. 85, No. 16, Aug. 20, 2013 (Aug. 20, 2013), pp. 7941-7947, XP055272748, ISSN: 0003-2700, DOI:10.1021/ac401715k abstract (7 pages).
Bin-Cheng Yin et al., "Sensitive Detection of MicroRNA in Complex Biological Samples via Enzymatic Signal Amplification Using DNA Polymerase Coupled with Nicking Endonuclease" Analytical Chemistry, vol. 85, No. 23, Dec. 3, 2013 (Dec. 3, 2013), pp. 11487-11493, XP055272740, ISSN: 0003-2700, DOI: 10.1021/ac403302a abstract (7 pages).
Lai et al., "Calibration Curves for Real-Time PCR", Clinical Chemistry 51:7, pp. 1132-1136, 2005, Molecular Diagnostics and Genetics.
International Search Report and Written Opinion of PCT Patent Application No. PCT/IB2015/002141, dated Apr. 6, 2016, 8 pages.
International Bureau, "International Preliminary Report on Patentability", issued in connection with Application No. PCT/IB2015/002141, dated Apr. 18, 2017, 6 pages.
International Bureau, "International Preliminary Report on Patentability", issued in connection with Application No. PCT/IB2015/002145, dated Apr. 18, 2017, 10 pages.
Stratagene Catalog, p. 39 (1988).

* cited by examiner

SEQUENCE LISTING

<160> NUMBER OF SEQ ID NOS: 31

<210> SEQ ID NO 1
<211> LENGTH: 72
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (72)..(72)
<223> OTHER INFORMATION: 3' - inverted thymidine

<400> SEQUENCE: 1
tgatagccct gtacaaatgc tgctcagaga tccattgtac agggctatca ctgttcctgc    60
tgaactgagc ca                                                        72

<210> SEQ ID NO 2
<211> LENGTH: 18
<212> TYPE: DNA
<213> ORGANISM: Artificial Sequence
<220> FEATURE:
<223> OTHER INFORMATION: Synthetic

<400> SEQUENCE: 2
tgatagccct gtacaatg                                                  18

<210> SEQ ID NO 3
<211> LENGTH: 13
<212> TYPE: DNA
<213> ORGANISM: Artificial Sequence
<220> FEATURE:
<223> OTHER INFORMATION: Synthetic

<400> SEQUENCE: 3
ctgctcagag atc                                                       13

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
cattgtacag ggctatca                                                  18

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
ctgttcctgc tgaactgagc ca          22

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
tggctcagtt cagcaggaac ag          22

<210> SEQ ID NO 7
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (54)..(54)
<223> OTHER INFORMATION: 3' - inverted thymidine

<400> SEQUENCE: 7
tgatagccct gtacaatgct gctcagagat ccctgttcct gctgaactga gcca          54

<210> SEQ ID NO 8
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' end FAM modification
<220> FEATURE:
<221> NAME/KEY: misc_feature
<222> LOCATION: (33)..(33)
<223> OTHER INFORMATION: 3'-end DABCYL modification

<400> SEQUENCE: 8
cgcgatgata gccctgtaca atgctgcttc gcg          33

<210> SEQ ID NO 9
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (74)..(74)
<223> OTHER INFORMATION: 3' - inverted thymidine

<400> SEQUENCE: 9
tgatagccct gtacaatgct gctcagagat ccagcattgt acagggctat cactgttcct          60
gctgaactga gcca          74

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
agcattgtac agggctatca          20

```
<210> SEQ ID NO 11
<211> LENGTH: 65
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (65)..(65)
<223> OTHER INFORMATION: 3' - inverted thymidine

<400> SEQUENCE: 11
tgatagccct gtacaatgct gctcagagat cccagggcta tcactgttcc tgctgaactg      60
agcca                                                                  65

<210> SEQ ID NO 12
<211> LENGTH: 11
<212> TYPE: DNA
<213> ORGANISM: Artificial Sequence
<220> FEATURE:
<223> OTHER INFORMATION: Synthetic

<400> SEQUENCE: 12
cagggctatc a                                                           11

<210> SEQ ID NO 13
<211> LENGTH: 65
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (65)..(65)
<223> OTHER INFORMATION: 3' - inverted thymidine

<400> SEQUENCE: 13
tgatagccct gtacaatgcc tcagccattg tacagggcta tcactgttcc tgctgaactg      60
agcca                                                                  65

<210> SEQ ID NO 14
<211> LENGTH: 18
<212> TYPE: DNA
<213> ORGANISM: Artificial Sequence
<220> FEATURE:
<223> OTHER INFORMATION: Synthetic

<400> SEQUENCE: 14
tgatagccct gtacaatg                                                    18

<210> SEQ ID NO 15
<211> LENGTH: 7
<212> TYPE: DNA
<213> ORGANISM: Artificial Sequence
<220> FEATURE:
<223> OTHER INFORMATION: Synthetic

<400> SEQUENCE: 15 cctcagc                                                                 7

<210> SEQ ID NO 16
<211> LENGTH: 18
<212> TYPE: DNA
<213> ORGANISM: Artificial Sequence
<220> FEATURE:
```

<223> OTHER INFORMATION: Synthetic

<400> SEQUENCE: 16
cattgtacag ggctatca                                                         18

<210> SEQ ID NO 17
<211> LENGTH: 63
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (63)..(63)
<223> OTHER INFORMATION: 3' - inverted thymidine

<400> SEQUENCE: 17
tgatagccct gtacaatgcc tcagcttgta cagggctatc actgttcctg ctgaactgag          60
cca                                                                         63

<210> SEQ ID NO 18
<211> LENGTH: 16
<212> TYPE: DNA
<213> ORGANISM: Artificial Sequence
<220> FEATURE:
<223> OTHER INFORMATION: Synthetic

<400> SEQUENCE: 18
ttgtacaggg ctatca                                                           16

<210> SEQ ID NO 19
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (60)..(60)
<223> OTHER INFORMATION: 3' - inverted thymidine

<400> SEQUENCE: 19
tgatagccct gtacaatgcc tcagctacag ggctatcact gttcctgctg aactgagcca          60

<210> SEQ ID NO 20
<211> LENGTH: 13
<212> TYPE: DNA
<213> ORGANISM: Artificial Sequence
<220> FEATURE:
<223> OTHER INFORMATION: Synthetic

<400> SEQUENCE: 20
tacagggcta tca                                                              13

<210> SEQ ID NO 21
<211> LENGTH: 84
<212> TYPE: RNA
<213> ORGANISM: Homo sapiens
<220> FEATURE:
<221> NAME/KEY: misc_feature
<222> LOCATION: (1)..(84)
<223> OTHER INFORMATION: miR-17

<400> SEQUENCE: 21
gucagaauaa ugucaaagug cuuacagugc agguagugau augugcaucu acugcaguga          60
aggcacuugu agcauuaugg ugac                                                  84

```
<210> SEQ ID NO 22
<211> LENGTH: 82
<212> TYPE: RNA
<213> ORGANISM: Homo sapiens
<220> FEATURE:
<221> NAME/KEY: misc_feature
<222> LOCATION: (1)..(82)
<223> OTHER INFORMATION: miR-19

<400> SEQUENCE: 22
gcaguccucu guuaguuuug cauaguugca cuacaagaag aauguaguug ugcaaaucua    60
ugcaaaacug augguggccu gc                                            82

<210> SEQ ID NO 23
<211> LENGTH: 72
<212> TYPE: RNA
<213> ORGANISM: Homo sapiens
<220> FEATURE:
<221> NAME/KEY: misc_feature
<222> LOCATION: (1)..(72)
<223> OTHER INFORMATION: miR-21

<400> SEQUENCE: 23
ugucggguag cuuaucagac ugauguugac uguugaaucu cauggcaaca ccagucgaug    60
ggcugucuga ca                                                       72

<210> SEQ ID NO 24
<211> LENGTH: 65
<212> TYPE: RNA
<213> ORGANISM: Homo sapiens
<220> FEATURE:
<221> NAME/KEY: misc_feature
<222> LOCATION: (1)..(65)
<223> OTHER INFORMATION: miR-155

<400> SEQUENCE: 24
cuguuaaugc uaaucgugau aggggguuuuu gccuccaacu gacuccuaca uauuagcauu    60
aacag                                                               65

<210> SEQ ID NO 25
<211> LENGTH: 96
<212> TYPE: RNA
<213> ORGANISM: Homo sapiens
<220> FEATURE:
<221> NAME/KEY: misc_feature
<222> LOCATION: (1)..(96)
<223> OTHER INFORMATION: miR-569

<400> SEQUENCE: 25
gguauuguua gauuaauuuu gugggacauu aacaacagca ucagaagcaa caucagcuuu    60
aguuaaugaa uccuggaaag uuaagugacu uuauuu                             96

<210> SEQ ID NO 26
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: hsa-miR-24

<400> SEQUENCE: 26
uggcucaguu cagcaggaac ag                                            22
```

```
<210> SEQ ID NO 27
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: hsa-miR-107

<400> SEQUENCE: 27
agcagcauug uacagggcua uca                                              23

<210> SEQ ID NO 28
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: hsa-miR-221

<400> SEQUENCE: 28
agcuacauug ucugcugggu uuc                                              23

<210> SEQ ID NO 29
<211> LENGTH: 84
<212> TYPE: RNA
<213> ORGANISM: Homo sapiens
<220> FEATURE:
<221> NAME/KEY: misc_feature
<222> LOCATION: (1)..(84)
<223> OTHER INFORMATION: hsa-miR-500

<400> SEQUENCE: 29 gcuccccuc ucuaauccuu gcuaccuggg ugagagugcu gucugaaugc aaugcaccug        60
ggcaaggauu cugagagcga gagc                                             84

<210> SEQ ID NO 30
<211> LENGTH: 81
<212> TYPE: RNA
<213> ORGANISM: Homo sapiens
<220> FEATURE:
<221> NAME/KEY: misc_feature
<222> LOCATION: (1)..(81)
<223> OTHER INFORMATION: hsa-miR-106a

<400> SEQUENCE: 30
ccuuggccau guaaaagugc uuacagugca gguagcuuuu ugagaucuac ugcaauguaa       60
gcacuucuua cauuaccaug g                                                81

<210> SEQ ID NO 31
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' - end FAM modification
```

```
<220> FEATURE:
<221> NAME/KEY: misc_feature
<222> LOCATION: (29)..(29)
<223> OTHER INFORMATION: 3' - end DABCYL modification

<400> SEQUENCE: 31
cgatgatagc cctgtacaat gcctcatcg                                    29
```

COVERED SEQUENCE CONVERSION DNA AND DETECTION METHODS

CROSS REFERENCE TO RELATED APPLICATIONS

This application claims priority to U.S. Provisional Patent Application Ser. No. 61/927,710, filed Jan. 15, 2014, which is incorporated herein by reference in its entirety.

FUNDING

At least a portion of the research disclosed herein was supported by a grant from the Japan Science and Technology Agency (JST), an agency of the Government of Japan.

BACKGROUND

The detection of target nucleic acid in test samples is important in various fields, including medicine and biology. Many compositions and procedures are available for the detection of specific nucleic acid molecules. Typically, this technology is based on sequence-dependent hybridization between a target nucleic acid and a nucleic acid probe which may range in length from short oligonucleotides (20 bases or less) to many kilobases (kb).

One widely used method for amplification of specific sequences from within a population of nucleic acid sequences is the polymerase chain reaction (PCR). In a typical PCR reaction, a target nucleic acid is amplified in three distinct steps: dissociation (denaturation) of a double-stranded template DNA into single strands; annealing of primers to the single-stranded template DNAs; and synthesis (extension) of a complementary strand from each primer. During PCR, the denaturation process, the annealing process, and the extension process are each carried out at different temperatures and are repeatedly cycled through the different reaction temperatures with a thermal cycler. Consequently, expensive temperature cycle control equipment is necessary to perform such a reaction, which prevents its routine use in field examinations, point-of-care (bedside) diagnoses, and inexpensive examinations.

Moreover, since the PCR reaction is carried out at three different temperatures, the reaction can be associated with challenges such as difficulty in maintaining accurate temperatures and that the time loss increases in proportion to the number of cycles. Further, the denaturation of a double-stranded template DNA into single strands requires the use of high temperatures, which necessitates that the reaction be performed using a limited number of thermostable DNA polymerases.

Accordingly, the following disclosure provides alternative methods and compositions for detecting a nucleic acid (such as DNA or RNA) under reaction conditions that are less rigorous than those used in PCR, while maintaining selectivity and sensitivity adequate to allow for the detection of nucleic acid molecules having a short length and at low concentrations. Among other aspects, the present disclosure provides novel methods and nucleic acid molecules that can improve the detection limit of target nucleic acids in a sample under low temperature, isothermal conditions, and can simplify or improve sample preparation and automated methods of detection.

SUMMARY OF THE INVENTION

In one aspect, the disclosure relates to a method for detecting a target nucleic acid in a sample, said method comprising contacting said sample with: a hairpin oligonucleotide comprising, in the 5' to 3' direction, a first arbitrary sequence, an endonuclease recognition site, a sequence complementary to said first arbitrary sequence, a sequence complementary to the 3' end of a target nucleic acid, and a 3'-end modification; a polymerase; and an endonuclease for a nicking reaction. In embodiments of this aspect, the method also comprises determining the presence or absence of a signal DNA, wherein the presence of the signal DNA indicates the presence of the target nucleic acid in the sample.

In embodiments of this aspect the polymerase may have strand displacement activity. In further embodiments, the polymerase may be 3' to 5' exonuclease deficient, 5' to 3' exonuclease deficient, or both 3' to 5' exonuclease deficient and 5' to 3' exonuclease deficient. In some embodiments the polymerase comprises a DNA polymerase.

In embodiments, the endonuclease may comprise a nicking endonuclease or a restriction endonuclease that can be used in a reaction that nicks an oligonucleotide.

The aspects and embodiments relating to the method described herein may be performed under isothermal conditions or under substantially constant temperatures. In further embodiments the method may be performed at temperatures that are lower than temperatures used in standard PCR methods. As one example, some embodiments of the method can be performed at temperatures at or below the melting temperature of the hairpin structure in an oligonucleotide (e.g., a CSC DNA, such as illustrated in the exemplary depiction in FIG. 1). In some embodiments, the method may be performed at a temperature at or below a calculated optimal hybridization or annealing temperature, or an experimentally determined hybridization or annealing temperature, of the target nucleic acid (T) and the oligonucleotide disclosed herein (e.g., CSC DNA). In embodiments, the method may be performed at a temperature that is below the melting temperature of the target nucleic acid (T) bound to the oligonucleotide disclosed herein (e.g., CSC DNA). In yet other embodiments, the method may be performed at temperatures that allow for polymerase and/or endonuclease activity. In further embodiments, the method may be performed at temperatures that are at or about the optimal reaction temperature for the polymerase and/or endonuclease present in the reaction mixture for the detection of a target nucleic acid in a sample.

In another aspect, the disclosure relates to an oligonucleotide (or a covered sequence conversion DNA or CSC DNA) comprising a hairpin structure, wherein the oligonucleotide comprises, in the 5' to 3' direction, a first arbitrary sequence, an endonuclease recognition site, a sequence complementary to said first arbitrary sequence, a sequence complementary to the 3' end of a target nucleic acid, and a 3'-end modification, wherein at least a portion of said first arbitrary sequence and at least a portion of said sequence complementary to said first arbitrary sequence hybridize to form said hairpin structure. In some embodiments of this aspect, the endonuclease recognition site is located in the loop of said hairpin structure. In some embodiments the endonuclease recognition site comprises a sequence that is complementary to a sequence that is nicked by an endonuclease. In other embodiments, the sequence that is nicked by the endonuclease is adjacent (downstream or upstream) to the sequence that is specifically recognized by the endonuclease. The target nucleic acid sequence may be any nucleotide sequence of interest and in some embodiments may comprise a sequence that originates from an infectious agent or a micro-RNA. In other embodiments the target nucleic acid may comprise a sequence from a gene that may be associated with a disease or a disorder.

In a further aspect, the disclosure relates to a composition for detecting a target nucleic acid in a sample, said composition comprising: an oligonucleotide comprising a hairpin structure, wherein the oligonucleotide comprises, in the 5' to 3' direction, a first arbitrary sequence, an endonuclease recognition site, a sequence complementary to said first arbitrary sequence, a sequence complementary to the 3' end of a target nucleic acid, and a 3'-end modification, wherein at least a portion of said first arbitrary sequence and at least a portion of said sequence complementary to said first arbitrary sequence hybridize to form said hairpin structure. The compositions can also comprise a polymerase, and/or an endonuclease capable of nicking at or adjacent to the endonuclease recognition site of the oligonucleotide when the endonuclease recognition site is double stranded. Compositions can also include other reagents such as reaction buffers, deoxyribonucleotides, and reporter molecules such as, for example, fluorophore-modified probe DNAs (e.g., molecular beacon probes) for the fluorescent detection of newly synthesized DNA.

In yet another aspect, the disclosure relates to a kit for detecting a target nucleic acid in a sample, said kit comprising: an oligonucleotide comprising a hairpin structure, wherein the oligonucleotide comprises, in the 5' to 3' direction, a first arbitrary sequence, an endonuclease recognition site, a sequence complementary to said first arbitrary sequence, a sequence complementary to the 3' end of a target nucleic acid, and a 3'-end modification, wherein at least a portion of said first arbitrary sequence and at least a portion of said sequence complementary to said first arbitrary sequence hybridize to form said hairpin structure. In embodiments the kits can further comprise a polymerase and/or an endonuclease capable of nicking an endonuclease recognition site or a site adjacent to the endonuclease recognition site. The kits can also include reagents such as reaction buffers, deoxyribonucleotides, and reporter molecules such as, for example, fluorophore-modified probe DNAs (e.g., molecular beacon probes) for the fluorescent detection of newly synthesized DNA such as a signal DNA. The kits can also comprise instructions for use in the practice of any one of the methods disclosed herein.

The methods, oligonucleotides, compositions, and kits disclosed herein may be used in combination with integrated system platforms. For example, methods, oligonucleotides, compositions, and kits of the present invention may be used in combination Abbott's ARCHITECT system. The methods, oligonucleotides, compositions, and kits disclosed herein may be used with sample preparation system platforms such as, for example, the m2000sp sample preparation system (Abbott Diagnostics, Abbott Park, Ill.). Similarly, the methods, oligonucleotides, compositions, and kits disclosed herein may be used with point-of-care system platforms such as, for example, Abbott's i-STAT point-of-care system (Abbott Diagnostics, Abbott Park, Ill.). Further, the methods, oligonucleotides, compositions, and kits of the present invention can be used with any number of other devices, assay platforms, and instrumentation such as, for example, hand held fluorescence detectors, micro-pH meters, microfluidic devices, microarrays, enzymatic detection systems, immunochromatographic strips, and lateral flow devices.

The methods, oligonucleotides, compositions, and kits disclosed herein may be used in the field of molecular diagnostics, including diagnosis of non-infectious and infectious diseases. For example, methods, oligonucleotides, compositions, and kits of the present invention can be used to detect micro-RNAs (miRNAs) associated with disease in humans. Non-limiting examples of miRNAs include hsa-miR-24 (SEQ ID NO:26), hsa-miR-107 (SEQ ID NO:27), hsa-miR-21 (SEQ ID NO:23), hsa-miR-500 (SEQ ID NO:29), hsa-miR-106a (SEQ ID NO:30) and hsa-miR-221 (SEQ ID NO:28). Similarly, methods, oligonucleotides, compositions, and kits of the present invention can be used to detect target nucleic acids originating from infectious diseases such as, for example, hepatitis B virus, hepatitis C virus, human immunodeficiency virus, *Chlamydia trachomatis, Neisseria gonorrhoeae*, influenza A virus, influenza B virus, and respiratory syncytial virus.

Additional aspects, embodiments, and advantages provided by the disclosure will become apparent in view of the description that follows.

DETAILED DESCRIPTION

Figure 1:
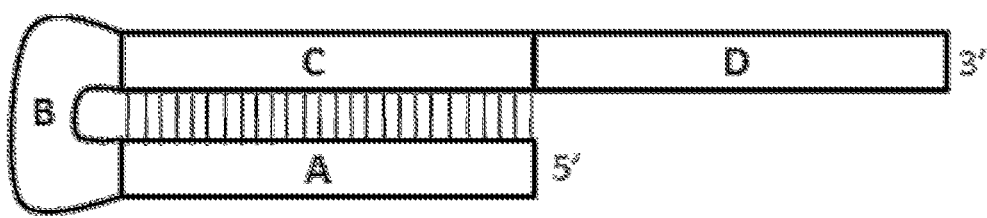
FIG. 1 is a diagram schematically illustrating a non-limiting example of a Covered Sequence Conversion DNA (CSC DNA) for the detection of a target nucleic acid in a sample. The CSC DNA comprises, in the 5' to 3' direction, an arbitrary sequence (A), an endonuclease recognition site (B) that can be used in a nicking reaction, a sequence (C) complementary to the arbitrary sequence, and a sequence (D) complementary to the target nucleic acid. The vertical lines between (A) and (C) indicate some amount of hybridization between the two regions.

In a general sense, the disclosure relates to nucleic acid constructs that are surprisingly effective in the detection of target nucleic acids in a test sample. The constructs disclosed herein comprise a nucleic acid sequence that allows the constructs to adopt structures that can avoid interaction or binding events between the constructs and signal DNAs that are generated in the presence of a target nucleic acid. The methods and nucleic acid constructs disclosed herein provide for selective and sensitive detection of target nucleic acids advantageously under low temperature and isothermal conditions.

In one aspect, the present invention relates to novel oligonucleotide constructs (referred to herein as a covered sequence conversion DNA or CSC DNA) that are useful in detecting a target nucleic acid in a sample. As depicted by the illustrative embodiment of FIG. 1, a CSC DNA can comprise a hairpin structure (or stem loop structure) having, in the 5' to 3' direction, an arbitrary sequence (A), an endonuclease recognition site (B), a sequence (C) complementary to the arbitrary sequence (A), and a sequence (D) complementary to the 3' end of a target nucleic acid.

The CSC DNA disclosed herein comprises an arbitrary sequence (A). The arbitrary sequence (A) in the CSC DNA can comprise any desired nucleic acid sequence and is not limited by any particular sequence. As discussed in greater detail below, the arbitrary sequence (A) provides at least a portion of the template for a signal DNA (e.g., (F) in FIG. 2), the production of which indicates the presence of target nucleic acid. Also as discussed herein, the sequence (A) provides at least a portion of a sequence that may hybridize to a complementary sequence comprised in sequence (C). The arbitrary sequence (A) in the CSC DNA is not limited by length. In some embodiments, the arbitrary sequence (A) in the CSC DNA is from about 5 to about 100 nucleic acid bases, and all integers between 5 and 100. In embodiments, the arbitrary sequence (A) in the CSC DNA is from about 5 to about 30 nucleic acid bases, and all integers between 5 and 30. In some embodiments, the arbitrary sequence (A) in the CSC DNA is from about 10 to about 30 nucleic acid bases, and all integers between 10 and 30. In yet further embodiments, the arbitrary sequence (A) in the CSC DNA is from about 15 to about 30 nucleic acid bases, and all integers between 15 and 30.

The CSC DNA comprises an endonuclease recognition site (B). In single stranded form (e.g., the hairpin structure of FIG. 1) the endonuclease recognition site (B) may comprises a sequence that is complementary to a sequence that may be nicked by an endonuclease. The sequence that is nicked by the endonuclease may be within, downstream, or upstream from the sequence that is recognized by the endonuclease. Suitably, when double stranded, the endonuclease recognition site (B) can be recognized by an endonuclease present in the reaction, and the endonuclease recognition site (B) (or a sequence adjacent to the endonuclease recognition site (B)) may be cleaved on only one strand of the double-stranded DNA (i.e., nicked). As described in greater detail below, binding of a target nucleic acid to the CSC DNA primes replication via DNA polymerase to create an active, double-stranded form of the endonuclease recognition site (B) that can serve as a recognition site for an endonuclease. Endonuclease nicking at the newly created double-stranded endonuclease site (B), or at a site adjacent to newly created double-stranded endonuclease site (B), then primes replication via DNA polymerase and generates signal DNA (see, e.g., FIG. 2). As illustrated in FIG. 2, the endonuclease recognition site (B) is oriented such that the newly replicated strand is nicked, not the CSC DNA. That is, when the newly replicated strand is generated the orientation of the endonuclease recognition site in B directs endonuclease activity (cleavage) of the newly replicated strand. As such, the endonuclease recognition site comprises a sequence that is complementary to a sequence that is nicked by an endonuclease, allowing the CSC oligonucleotide to remain intact throughout the reaction (i.e., the CSC DNA is not nicked or cleaved).

The CSC DNA comprises a sequence (C) complementary to the arbitrary sequence (A). As disclosed herein, at least a portion of the sequence (C) hybridizes to at least a portion of the complementary region of arbitrary sequence (A) and forms a hairpin (or stem loop) structure. See, e.g., FIG. 1. As illustrated in the non-limiting embodiment of FIG. 1, the double stranded stem is flanked on one side by an unpaired loop region comprising the endonuclease recognition site (B), and on the other end by the sequence (D) complementary to a target nucleic acid.

The sequence (C) is not limited by length, and can be from about 5 to about 100 nucleic acid bases, and all integers between 5 and 100. In some embodiments, the sequence (C) is from about 5 to about 30 nucleic acid bases, and all integers between 5 and 30. In some embodiments, the sequence (C) in the CSC DNA is from about 10 to about 30 nucleic acid bases, and all integers between 10 and 30. In yet further embodiments, the sequence (C) is from about 15 to about 30 nucleic acid bases, and all integers between 15 and 30. The sequence (C) is also not required to be the same length as the arbitrary sequence (A). In some embodiments, the sequence (C) can be the same length as the arbitrary sequence (A), or it can be about 1-20 or about 1-10 bases shorter than the arbitrary sequence (A). The stem structure of the CSC DNA may generally comprises a length of double stranded DNA ranging from about 3 to about 60 nucleic acid base pairs in length. In some embodiments, the stem comprises a length of double stranded DNA ranging from about 5 to about 20 nucleic acid base pairs, and all integers between 5 and 20.

The stem can also include bulges or mismatches, and sequence (C) does not have to be 100% complementary to sequence (A). In some embodiments, the sequence (C) may be 100% complementary to all of, or to portions of, the arbitrary sequence (A). For example, sequence (C) can be greater than about 50%, 60%, 70%, 80%, or 90% complementary to sequence (A). Despite mismatches, the two sequences generally have the ability to selectively hybridize to one another under appropriate conditions. In some embodiments, the amount of complementarity between sequence (A) and sequence (C) is from about 80% to 100%, which can allow for hybridization under stringent or highly stringent conditions such as, for example, conditions disclosed herein.

In some embodiments, the double stranded stem of the stem-loop structure, for example, portions of sequences (A) and (C), of a CSC DNA can have a GC content that ranges from about 20% to about 70%, including any percentage between 20% and 70%.

Figure 2:
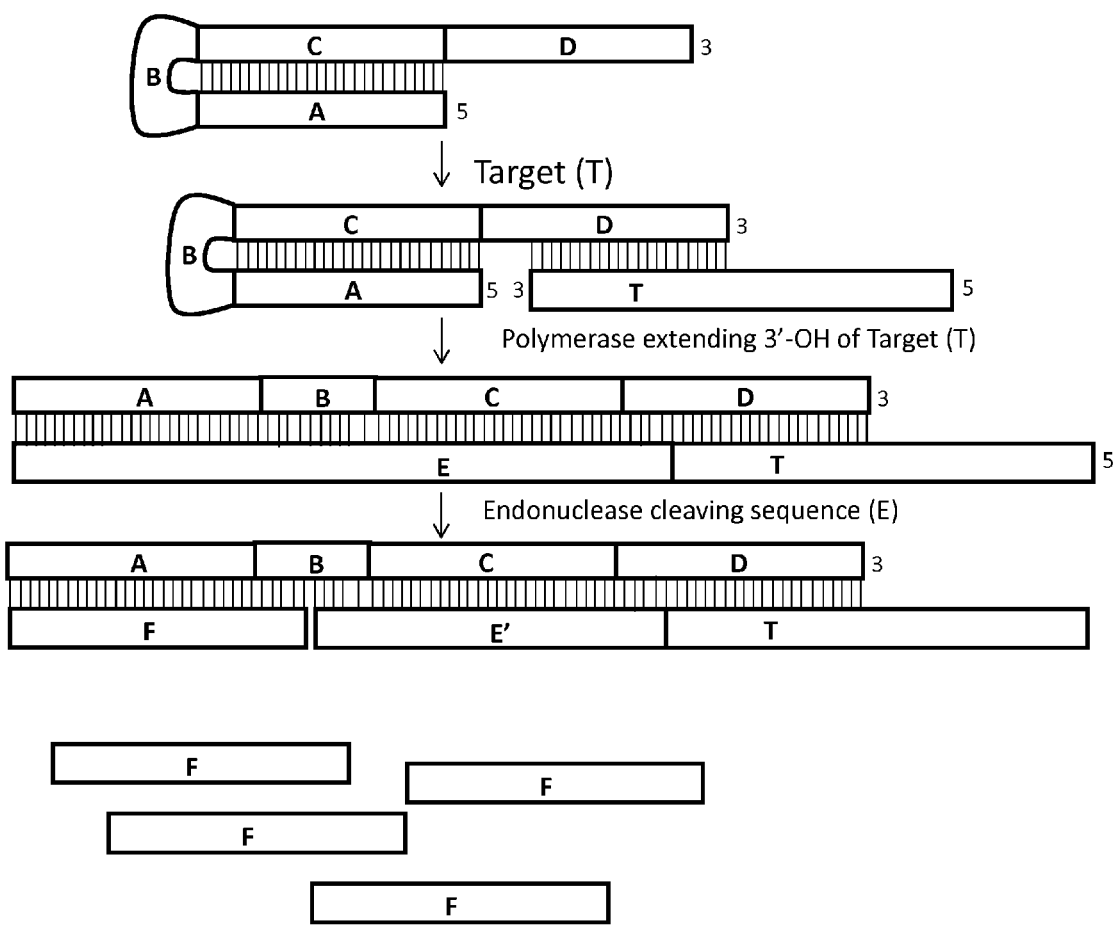
FIG. 2 is a diagram schematically illustrating the progression of an exemplary reaction for the detection of a target nucleic acid in a sample, with sequences (A)-(D) as described in FIG. 1, sequence (T) representing a target sequence, sequence (E) representing an extension sequence, sequence (E') representing a nicked extension sequence, and sequence (F) representing signal sequence.

In some embodiments, at least a portion of the endonuclease recognition site (B) is located in the single stranded loop of the stem loop structure (e.g., FIG. 1). In some embodiments, the entire endonuclease recognition site (B) is located in the sequence comprising the loop region. Generally, the loop in the stem loop structure can be from about 3 to about 30 nucleotide bases and any number in between. In some embodiments, the endonuclease recognition site (B) is from 4 to about 10 nucleotide bases in length and all integers between 4 and 10.

Sequence (D) of the CSC DNA (see, e.g., FIG. 1) is complementary to at least a portion of the 3' end sequence of the target nucleic acid, and can have a length ranging from about 5 to about 100 nucleic acid bases, including any integer between 5 and 100. In some embodiments, sequence (D) is from about 5 to about 30 nucleic acid bases, and all integers between 5 and 30. In some embodiments, the sequence (D) in the CSC DNA is from about 10 to about 30 nucleic acid bases in length and all integers between 10 and 30. In yet further embodiments, the sequence (D) in the CSC DNA is from about 15 to about 30 nucleic acid bases in length and all integers between 15 and 30.

The sequence (D) can be 100% complementary to the 3' end sequence of the target nucleic acid. In some embodiments, the sequence (D) can be less than 100% complementary to the 3' end sequence of the target nucleic acid and can range, for example, from about 50% to about 99% complementary to the 3' end sequence of the target nucleic acid. In still other embodiments, the sequence (D) can be from about 80% to 100% (including all percentages between 80% and 100%) complementary to the 3' end sequence of the target nucleic acid.

Complementary sequences are capable of forming hydrogen bonding interactions to form a double stranded nucleic acid structure (e.g., nucleic acid base pairs). For example, a sequence that is complementary to a first sequence includes a sequence which is capable of forming Watson-Crick base-pairs with the first sequence. As used herein, the term "complementary" does not require that a sequence is complementary over the full-length of its complementary strand, and encompasses a sequence that is complementary to a portion of another sequence. Thus, in some embodiments, a complementary sequence encompasses sequences that are complementary over the entire length of the sequence or over a portion thereof. For example, two sequences can be complementary to each other over a length ranging from about 2 to about 100 consecutive (contiguous) nucleotides, or any integer between 2 and 100. In some embodiments, two sequences can be complementary to each other over a length ranging from about 15 to about 30 consecutive (contiguous) nucleotides, or any integer between 15 and 30. As used herein, complementary sequences can encompass sequences that have some sequence mismatches. For example, complementary sequences can include sequences that are complementary to at least about 70% to 100%, preferably greater than above 95% of the length of the sequence. Despite some amount of mismatches, complementary sequences generally have the ability to selectively hybridize to one another under appropriate conditions such as, for example, stringent and highly stringent conditions such as those described herein.

The CSC DNA may be synthesized by known methods. For example, the CSC DNA can be synthesized using a phosphoramidite method, a phosphotriester method, an H-phosphonate method, or a thiophosphonate method.

The CSC DNA may comprise chemical modifications such as are generally known in the art. In some embodiments, for example, the CSC DNA can comprise chemically modified nucleic acids (e.g., 2'-O methyl derivative, phosphorothioates, etc.), 3' end modifications, 5' end modifications, or any combinations thereof. In some embodiments, the 3' end of the CSC DNA may be modified such that an extension reaction does not occur from the 3' end of the CSC DNA (e.g., upon binding of a target sequence, or another non-target sequence, having an overhang beyond the (D) sequence that might serve as a template for polymerase extension). As illustrated in FIG. 2, it is the 3' end of the target nucleic acid, not the CSC DNA, which initiates DNA replication that produces signal DNA. Any replication initiated from the 3' end of the CSC DNA may lead to detection errors (e.g., false positives). Further, non-specific extension reactions from an unmodified 3' end of the CSC DNA arising from events such as, for example, binding between the CSC DNA and a non-target sequence, binding between the CSC DNA and a target sequence at an incorrect position, or non-templated de novo or ab initio DNA synthesis may also lead to detection errors. Accordingly, in embodiments, the CSC DNA comprises a 3' end modification that can reduce the occurrence or entirely avoid the occurrence of any non-desired extension reactions, such as those discussed above. Non-limiting examples of 3'-end modifications include TAMRA, DABCYL, and FAM. Other non-limiting examples of modifications include, for example, biotinylation, fluorochromation, phosphorylation, thiolation, or amination.

In another aspect, the present invention encompasses methods for detecting a target nucleic acid in a sample. The methods generally comprise contacting the sample with: a CSC DNA as disclosed herein that comprises a sequence (D) complementary to the 3' end of the target nucleic acid; a polymerase; and an endonuclease.

The method comprises contacting a sample with an endonuclease. The endonuclease may be a nicking endonuclease or a restriction endonuclease that is capable of or that can be used in nicking the sequence complementary to the endonuclease recognition site (B) within the CSC DNA. In some embodiments, the endonuclease comprises a nicking endonuclease or a restriction endonuclease that can catalyze or can be used to catalyze a double-stranded DNA nicking reaction. In embodiments providing a nicking endonuclease, the phosphodiester linkage of one strand of a double-strand DNA may be cleaved to generate a phosphate group on the 5' side of the cleavage site and a hydroxyl group on the 3' side. Non-limiting examples of nicking endonucleases include Nb.BbvCI, Nt.AlwI, Nt.BbvCI, Nb.BsrDI, Nb.BtsI, Nt.BspQI, Nt.BstNBI, Nb.BsmI, Nt.CviPII, and Nt.BsmAI.

In some embodiments, the endonuclease may be a restriction endonuclease. In these embodiments the restriction endonuclease recognition site may be modified so that the restriction endonuclease cleaves the phosphodiester bond on only one strand of a double stranded DNA, and generates a nick in the double strand. Methods or strategies may be used to modify the activity of the restriction endonuclease such as, for example, including a chemical modification in at least one strand of a double-stranded nucleic acid that is not cleaved by the restriction enzyme. One non-limiting example of such a modification includes replacing the oxygen atom of phosphodiester linkage of one strand with a sulfur atom.

In embodiments providing a restriction endonuclease, the phosphodiester linkage of one strand of a double-strand DNA may be cleaved to generate a phosphate group on the 5' side of the cleavage site and a hydroxyl group on the 3' side. Non-limiting examples of restriction endonucleases include Hinc II, Hind II, Ava I, Fnu4HI, Tth111I and NciI.

The method comprises contacting a sample with a polymerase. In some embodiments, the polymerase may be a DNA polymerase having strand displacement activity. In some embodiments, the polymerase may be a polymerase that lacks 5'-3' exonuclease activity, lacks 3'-5' exonuclease activity, or lacks both 5'-3' and 3'-5' exonuclease activity. The polymerase may be eukaryotic, prokaryotic, or viral in origin, and can also be genetically modified. In some embodiments, the polymerase is selected from among those that function at lower temperatures, including ambient (e.g., room) temperatures. Non-limiting examples of DNA polymerases include Klenow fragments, DNA polymerase I derived from *E. coli*, 5' to 3' exonuclease-deficient Bst DNA polymerases derived from *Bacillus stearothermophilus*, and 5' to 3' exonuclease-deficient Bca DNA polymerases derived from *Bacillus* caldotenax.

One non-limiting embodiment of the methods disclosed herein is illustrated in FIG. 2. Briefly, a sample is contacted with a CSC DNA in the presence of a DNA polymerase and an endonuclease capable of nicking the double-stranded form (i.e., complementary sequence) of the endonuclease recognition site (B), or a site adjacent to the double-stranded form of the endonuclease recognition site (B). If a target nucleic acid (T) is present in the sample, the 3' end sequence of the target nucleic acid (T) hybridizes to the sequence (D) which is complementary to the target and primes or initiates strand displacement replication (by the DNA polymerase present in the reaction mixture) thereby generating double stranded extension sequence (E) that includes the double stranded endonuclease recognition site (B). Recognition of the newly-generated double stranded endonuclease recognition site (B) (by the endonuclease present in the reaction mixture), and subsequent nicking of the newly-generated strand (by the endonuclease present in the reaction mixture), generates oligonucleotide signal sequence (F) and extension sequence (E'). Because the 3'-OH of sequence (E') at the nick serves as an initiation site for subsequent rounds of strand displacement replication, oligonucleotide (F) is displaced from the CSC DNA by DNA polymerase which continues to replicate and amplify (F) in the reaction mixture.

Methods according to the invention may be performed under isothermal or substantially constant temperature conditions. In embodiments that relate to performing the method under a substantially constant temperature, some fluctuation in temperature is permitted. For example, in some embodiments a substantially constant temperature may fluctuate within a desired or identified target temperature range (e.g., about +/−2° C. or about +/−5° C.). In embodiments, a substantially constant temperature may include temperatures that do not include thermal cycling. In some embodiments, methods can be performed at isothermal or substantially constant temperatures such as, for example, (1) temperatures below the calculated/predicted or experimentally determined melting temperature of the CSC DNA's hairpin-loop structure; (2) temperatures at or below about the calculated/predicted or experimentally determined optimal hybridization or annealing temperature of the target nucleic acid (T) to sequence (D) of the CSC DNA; (3) temperatures at or below the melting temperature of the target nucleic acid (T) bound to CSC DNA (typically, hybridization or annealing temperatures are slightly below the melting temperature); or (4) temperatures at or about the calculated/predicted or experimentally determined optimal reaction temperature for the polymerase and/or endonuclease present in the reaction mixture.

The methods may comprise reaction temperatures that range from about 20° C. to about 70° C., including lower temperatures falling within the range of about 20° C. to about 42° C. In some embodiments, the reaction temperature range is from 35° C. to 40° C. (e.g., 35° C., 36° C., 37° C., 38° C., 39° C., or 40° C.). In other embodiments, the reaction temperature is below 65° C., including lower temperatures below about 55° C., 50° C., 45° C., 40° C., or about 30° C. In still other embodiments, reaction temperatures may be about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., or about 70° C.

The methods may be performed for a time that is adequate to allow for amplification of a detectable amount of signal sequence in the presence of a target nucleic acid. In some embodiments, the reaction time may range from about 10 minutes to 16 hours. In still other embodiments, the reaction time may range from about 10 to 120 minutes, or from about 15 to 60 minutes.

Throughout the specification, oligonucleotide (F) is also referred to as a signal DNA. Because signal DNA (F) is generated only in the presence of the target nucleic acid (T), methods according to the present invention detect the presence or absence of a target nucleic acid (T) in a sample by detecting the presence or absence of signal DNA (F). The signal DNA is not limited by sequence, and can be any sequence that is amenable to detection. The signal DNA is also not limited by length. Preferably, the signal DNA can be from about 5 to about 100 bases, and any integer between 5 and 100. In some embodiments, the signal DNA can be from about 5 to about 30 nucleic acid bases, and all integers between 5 and 30. In some embodiments, the signal DNA can be from about 10 to about 30 bases in length and all integers between 10 and 30. In yet further embodiments, the signal DNA can be from about 15 to about 30 bases in length and all integers between 15 and 30.

Methods according to the disclosure may be performed under buffer conditions that comprise a pH range from about 4 to about 10, or from about 7 to about 9. The buffer may comprise a salt concentration from about 10 mM to about 500 mM, or from about 50 mM to 150 mM. In some embodiments the method may be performed using an amount of CSC DNA that allows for amplification of a detectable amount of signal sequence in the presence of a target nucleic acid. In some embodiments, the CSC DNA concentration may range from about 1 nM to about 100 µM, from about 1 nM to about 150 nM, from about 5 nM to about 50 nM, or from about 5 nM to about 25 nM.

The presence of signal DNA can be detected by any method known in the art. For example, gel electrophoresis and staining with ethidium bromide can be used. Also, the presence of signal DNA can be detected using fluorescence polarization, immunoassay, fluorescence resonance energy transfer, enzyme labeling (such as peroxidase or alkaline phosphatase), fluorescent labeling (such as fluorescein or rhodamine), chemiluminescence, bioluminescence, surface plasmon resonance (SPR), or a fluorophore-modified probe DNA (e.g., TaqMan probe). The amplification product can also be detected by using a labeled nucleotide labeled with a biotin, for example. In such a case, the biotin in the amplification product can be detected using fluorescence-labeled avidin or enzyme-labeled avidin, for example. The amplification product can also be detected with electrodes by using redox intercalator known to those skilled in the art. The amplification product can also be detected using surface plasmon resonance (SPR), or using a Quarts Crystal Microbalance (QCM).

The methods according to the present invention detect the presence or absence of a target nucleic acid (T) in a sample. The target nucleic acid (e.g., (T) in FIG. 2) can comprise any nucleic acid sequence and can include DNA, RNA, chemically modified nucleic acids, non-natural nucleic acids, nucleic acid analogs, or any hybrid or combination thereof. Accordingly, in some embodiments, DNA may include cDNA, genomic DNA, and synthetic DNA, and RNA may include total RNA, mRNA, rRNA, siRNA, hnRNA, piRNA, aRNA, miRNA, and synthetic RNA. While some embodiments relate to particular target nucleic acid sequences, any nucleic acid sequence can be a target nucleic acid sequence to be detected. The disclosure provides for the detection of a target nucleic acid with selectivity and sensitivity even when the nucleic acid is a short-chain nucleic acid. Accordingly, the degree of complementarity between sequences (D) and (T) allows for specific hybridization between the sequences (e.g., the number of complementary nucleic acids in (D) and (T) sequences avoids non-specific hybridization under a given set of reaction conditions).

In embodiments, the target nucleic acid sequence can be from, or derived from any number of sources including, for example, genomic DNA, expressed mRNA, nucleic acid sequences from pathogens (microbes, viruses), or therapeutic nucleic acids. Accordingly, the CSC DNAs and the methods disclosed herein may be used for the diagnosis and prognosis of diseases (e.g., arising from genetic and infectious sources), identification of contaminants (e.g., foodborne illnesses, equipment contamination), personalized medicine (e.g., monitoring and/or prognosis of a therapy), and the like. For example, molecular diagnostic testing can be performed with respect to the following infectious diseases: Hepatitis B Virus (HBV); hepatitis C (HCV); HCV (genotypes 1-6); Human Immunodeficiency Virus type 1 (HIV-1); *Chlamydia trachomatis; Neisseria gonorrhoeae*; influenza A; influenza B; Respiratory Syncytial Virus (RSV).

In some embodiments, the target nucleic acid can comprise micro-RNAs (miRNA). Micro-RNAs include small non-coding RNA molecules of about 22 nucleotides. Micro-RNAs function in transcription and post-transcriptional regulation of gene expression. Micro-RNAs function by base pairing with complementary regions of messenger RNA (mRNA), resulting in gene silencing via translational repression or target degradation.

There are a number of human diseases associated with miRNA dysfunction, and methods, compositions, and kits according to the present invention can be used for diagnostic purposes. For example, miRNAs have been associated with cancers, e.g., a disease known to be associated with miRNA dysfunction is chronic lymphocytic leukemia. There are several other miRNAs known as oncomirs that are linked with cancers. Some examples include: miR-17 (SEQ ID NO.: 21); miR-19 (SEQ ID NO.: 22); miR-21 (SEQ ID NO.: 23); miR-155 (SEQ ID NO.: 24); and miR-569 (SEQ ID NO.: 25). Still other miRNAs have been associated with viral infections and eukaryotic response to bacterial pathogens. Studies have characterized changes in host micro-RNA expression following infection with exclusively extracellular (*Helicobacter pylori*) or intracellular (*Salmonella enterica*) Gram-negative bacteria, as well as in the response to Gram-positive (*Listeria monocytogenes*) and other pathogens (*Mycobacterium* and *Francisella* species). (*RNA Biol*. June; 9(6):742-50.) Other miRNAs of interest include without limitation: hsa-miR-24 (SEQ ID NO: 26); hsa-miR-107 (SEQ ID NO.: 27); and hsa-miR-221 (SEQ ID NO.: 28).

Any type of sample that may comprise a target nucleic acid may be used in the methods disclosed herein. As such, the sample containing or suspected of containing a target nucleic acid is not specifically limited, and includes, for example, biological samples derived from living subjects, such as whole blood, serum, buffy coat, urine, feces, cerebrospinal fluid, seminal fluid, saliva, tissue (such as cancerous tissue or lymph nodes), cell cultures (such as mammalian cell cultures or bacterial cultures); samples containing nucleic acids, such as viroids, viruses, bacteria, fungi, yeast, plants, and animals; samples (such as food and biological preparations) that may contain or be infected with microorganisms such as viruses or bacteria; and samples that may contain biological substances, such as soil, industrial process and manufacturing equipment, and wastewater. Furthermore, a sample may be processed by any known method to prepare a nucleic acid-containing composition used in the methods disclosed herein. Examples of such preparations can include cell breakage (e.g., cell lysates and extracts), sample fractionation, nucleic acids in the samples, and specific nucleic acid molecular groups such as mRNA-enriched samples. The sample used in the method for detecting a target nucleic acid of the present invention is not limited to those derived from biological and natural products as mentioned above and may be a sample containing a synthetic oligonucleotide.

Methods according to the present invention can be performed in combination with the Abbott m2000sp sample preparation system. The m2000sp uses magnetic particle technology to capture nucleic acids and washes the particles to remove unbound sample components. The bound nucleic acids are eluted and transferred to a 96 deep-well plate. The Abbott m2000sp can also combine with the washed nucleic acids transferred to the 96 deep-well plate any reagents required to perform the methods according to the present technology. For example, CSC DNAs, polymerases, endonucleases, molecular beacons, and any other reagent (e.g., dNTPs) can be added as required, or desired.

Methods according to the present invention can also be interfaced with point-of-care platforms. For example, the incorporation of a deoxyribonucleotide triphosphate (dNTP) into a growing DNA strand involves the formation of a covalent bond and the release of pyrophosphate and a positively charged hydrogen ion affecting the pH of a reaction. As such, the synthesis of signal DNA according to methods of the present invention can be detected by tracking changes in pH using, for example, point-of-care micro-pH meters. For example, Abbott's i-STAT point-of-care system can be supplied with single-use disposable cartridges containing micro fabricated sensors, calibration solutions, fluidic systems, and waste chambers for analysis of pH.

The methods disclosed herein can comprise additional reagents. Some non-limiting examples of other reagents that can be used in the nucleic acid amplification reaction include metallic salts such as sodium chloride, magnesium chloride, magnesium acetate, and magnesium sulfate; substrates such as dNTP mix; and buffer solutions such as Tris-HCl buffer, tricine buffer, sodium phosphate buffer, and potassium phosphate buffer. Furthermore, agents such as dimethyl sulfoxide and betaine (N,N,N-trimethylglycine); acidic substances described in International Publication No. WO 99/54455; and cationic complexes can be used.

The methods and nucleic acid structures provided herein may be used in methods that provide for exponential amplification of a signal DNA. For example, exponential amplification of a signal DNA was achieved using a sequence conversion DNA in combination with a second signal amplification DNA. See International application PCT/JP2011/078717 (Komiya), filed Dec. 12, 2011, and filed as U.S. patent application Ser. No. 13/992,058, which is incorporated by reference.

The Examples that follow are intended to be illustrative of the aspects and embodiments described above. Neither the above disclosure nor the Examples below should be viewed as limiting to the scope of the appended claims. One of skill in the art will appreciate that the disclosure is not limited by

Example 1

A reaction for detecting the presence of signal DNA in the presence and absence of target DNA was performed using the Covered Sequence Conversion DNA #1 represented by SEQ ID NO.: 1 (CSC DNA #1). A second reaction was performed using the Uncovered Sequence Conversion DNA #1 represented by SEQ ID NO.: 7 (USC DNA #1).

The target nucleic acid was human micro RNA hsa-miR-24 (SEQ ID NO.: 6). Both reactions were performed in a 25 µL reaction volume containing New England Biolabs (NEB) Buffer 2 having a final concentration of 10 mM Tris-HCl, 50 mM NaCl, 10 mM MgCl2, 1 mM DTT, pH 7.9. The nicking endonuclease used in the reaction was Nt.AIw1 at a concentration of 0.1 units/µL. The polymerase used in the reaction was Bst DNA Polymerase Large Fragment at a concentration of 0.08 units/µL. The dNTP's were present at a final concentration 200 µM each. CSC DNA #1 and USC DNA #1 were present in the reaction at a final concentration 100 nM. Molecular Beacon probes were used to detect the presence of signal DNA and were present at a final concentration of 100 nM.

CSC DNA #1 has the following sequence:

```
                                          (SEQ ID NO.: 1)
5'TGATAGCCCTGTACAAATGCTGCTCAGAGATCCATTGT

ACAGGGCTATCACTGTTCCTGCTGAACTGAGCCA3'-idT
```

CSC DNA #1 includes: an arbitrary sequence (A) (SEQ ID NO.: 2); a Nt.AlwI endonuclease recognition site (B) (SEQ ID NO.: 3) that can be used in a nicking reaction; a sequence (C) (SEQ ID NO.: 4) complementary to the arbitrary sequence (A) (SEQ ID NO.: 2); and a sequence (D) (SEQ ID NO.: 5) complementary to the target nucleic acid human micro RNA hsa-miR-24 (SEQ ID NO.: 6).

USC DNA #1 has the following sequence:

```
                                          (SEQ ID NO.: 7)
5'TGATAGCCCTGTACAATGCTGCTCAGAGATCCCTGTTC

CTGCTGAACTGAGCCA3'-idT
```

USC DNA #1 has in common with CSC DNA #1 the same arbitrary sequence (A) (SEQ ID NO.: 2), Nt.AlwI endonuclease recognition site (B) (SEQ ID NO.: 3), and sequence (D) (SEQ ID NO.: 5) complementary to the target nucleic acid human micro RNA hsa-miR-24 (SEQ ID NO.: 6). USC DNA #1 does not have a sequence (C) complementary to the arbitrary sequence (A), and therefore does not form a hairpin-loop structure as illustrated in FIG. 1.

Both CSC DNA #1 and USC DNA #1 have a 3' inverted thymidine modification (idT) to confer resistance to nucleolytic degradation. This modification will also prevent non-specific priming of DNA replication.

The target nucleic acid corresponds to human micro RNA hsa-miR-24 having the following sequence:

```
                                          (SEQ ID NO.: 6)
5' TGGCTCAGTTCAGCAGGAACAG 3'
```

To detect the presence of signal DNA in each reaction, the following molecular beacon was used:

```
                                          (SEQ ID NO.: 8)
5' (FAM)-CGCGATGATAGCCCTGTACAATGCTGCTTCG

CG-(DABCYL) 3'
```

Figure 3:
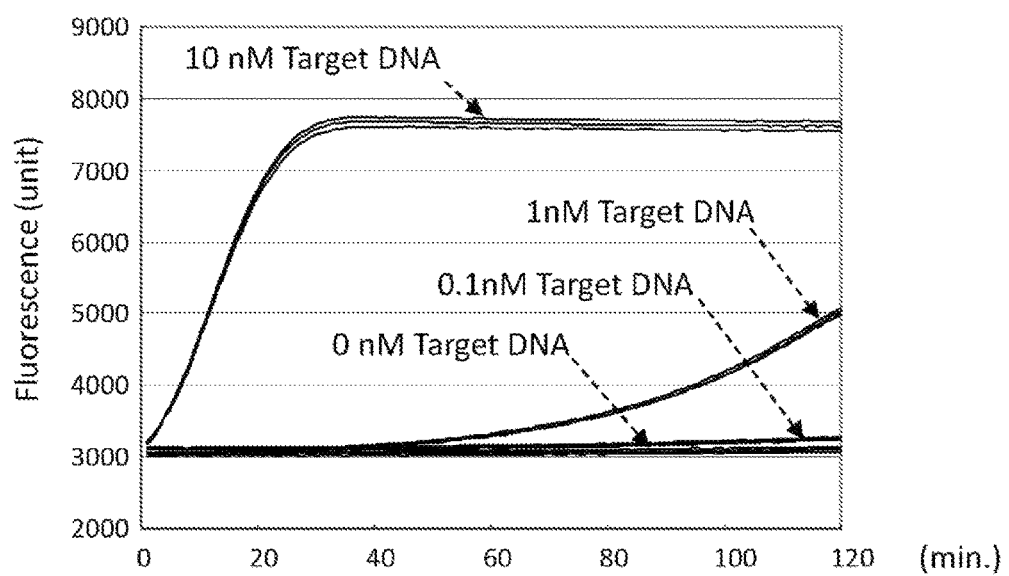
FIG. 3 depicts the results of reactions using CSC DNA #1 (SEQ ID NO.: 1) to detect different concentrations (10 nM, 1 nM, 0.1 nM, and 0.0 nM) of human micro RNA hsa-miR-24 target DNA (SEQ ID NO.: 6).
Figure 4:
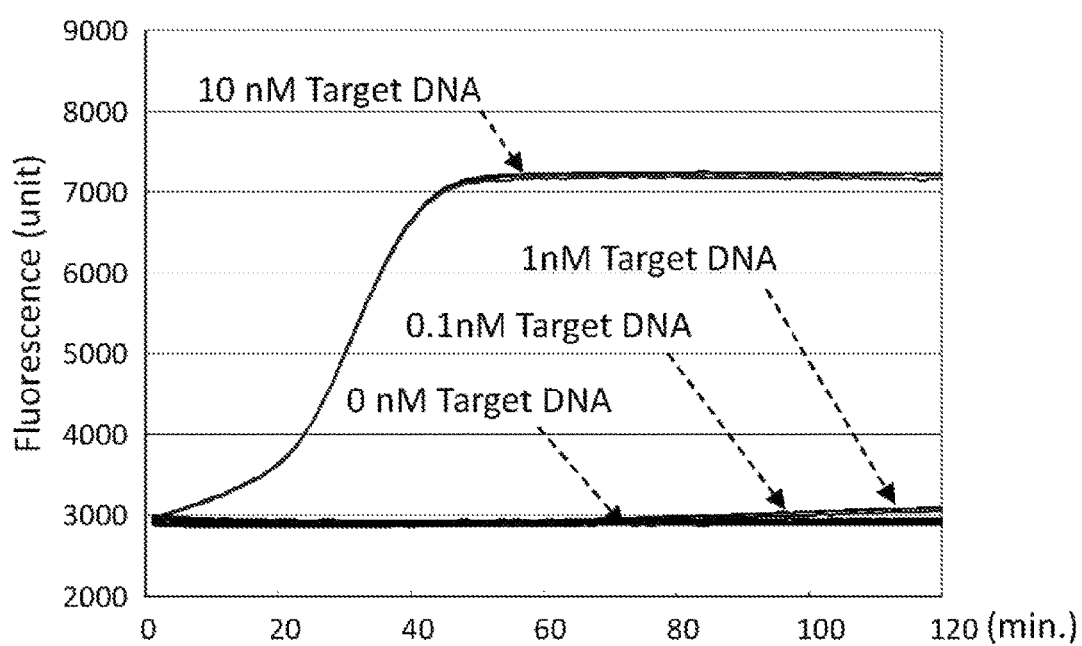
FIG. 4 depicts the results of reactions using Uncovered Sequence Conversion DNA (USC DNA) #1 (SEQ ID NO.: 7) to detect different concentrations (10 nM, 1 nM, 0.1 nM, and 0.0 nM) of human micro RNA hsa-miR-24 target DNA (SEQ ID NO.: 6).

The results of reactions using CSC DNA #1 to detect human micro RNA hsa-miR-24 target DNA (SEQ ID NO.: 6) at different concentrations (10 nM, 1 nM, 0.1 nM, and 0.0 nM) are shown in FIG. 3. The results of reactions using USC DNA #1 to detect target DNA present at different concentrations (10 nM, 1 nM, 0.1 nM, and 0.0 nM) are shown in FIG. 4. In FIGS. 3 and 4, the vertical axis shows the fluorescence intensity, and the horizontal axis shows time in minutes. Fluorescent measurements were performed at 37° C. at 1 minute intervals for 120 minutes using a Bio-Rad PCR system CFX 96.

Example 2

Reactions for detecting the presence of signal DNA in the presence and absence of target DNA were performed using the Covered Sequence Conversion DNA #3 represented by SEQ ID NO.: 9 (CSC DNA #2). The target nucleic acid was human micro RNA hsa-miR-24 (SEQ ID NO.:6).

The reactions were performed in a 25 µL reaction volume containing New England Biolabs (NEB) Buffer 2 having a final concentration of 10 mM Tris-HCl, 50 mM NaCl, 10 mM MgCl2, 1 mM DTT, pH 7.9. The nicking endonuclease used in the reaction was Nt.AIw1 present at a concentration of 0.1 units/µL. The polymerase used in the reaction was Bst DNA Polymerase Large Fragment present at a concentration of 0.08 units/µL. The dNTP's were present at a final concentration 200 µM each. CSC DNA #2 was present in the reaction at a final concentration 100 nM. A Molecular Beacon probe was used to detect the generation of signal DNA and was present at a final concentration of 100 nM.

CSC DNA #2 has the following sequence:

```
                                          (SEQ ID NO.: 9)
5'TGATAGCCCTGTACAATGCTGCTCAGAGATCCAGC

ATTGTACAGGGCTATCACTGTTCCTGCTGAACTGAGC

CA3'-idT
```

CSC DNA #2 includes: an arbitrary sequence (A) (SEQ ID NO.: 2); a Nt.AlwI endonuclease recognition site (B) (SEQ ID NO.: 3) that can be used in a nicking reaction; a sequence (C) (SEQ ID NO.: 10) complementary to the arbitrary sequence (A) (SEQ ID NO.: 2); and a sequence (D) (SEQ ID NO.: 5) complementary to the target nucleic acid human micro RNA hsa-miR-24 (SEQ ID NO.: 6). CSC DNA also has a 3'-end inverted thymidine modification.

The target nucleic acid corresponds to human micro RNA hsa-miR-24 having the following sequence:

```
                                          (SEQ ID NO.: 6)
5' TGGCTCAGTTCAGCAGGAACAG 3'
```

To detect the presence of signal DNA generated after binding of the human micro RNA hsa-miR-24 target DNA (SEQ ID NO.: 6) to the CSC DNA #2, the following molecular beacon was used:

```
                                          (SEQ ID NO.: 8)
5' (FAM)-CGCGATGATAGCCCTGTACAATGCTGCTTCG

CG-(DABCYL) 3'
```

Figure 5:
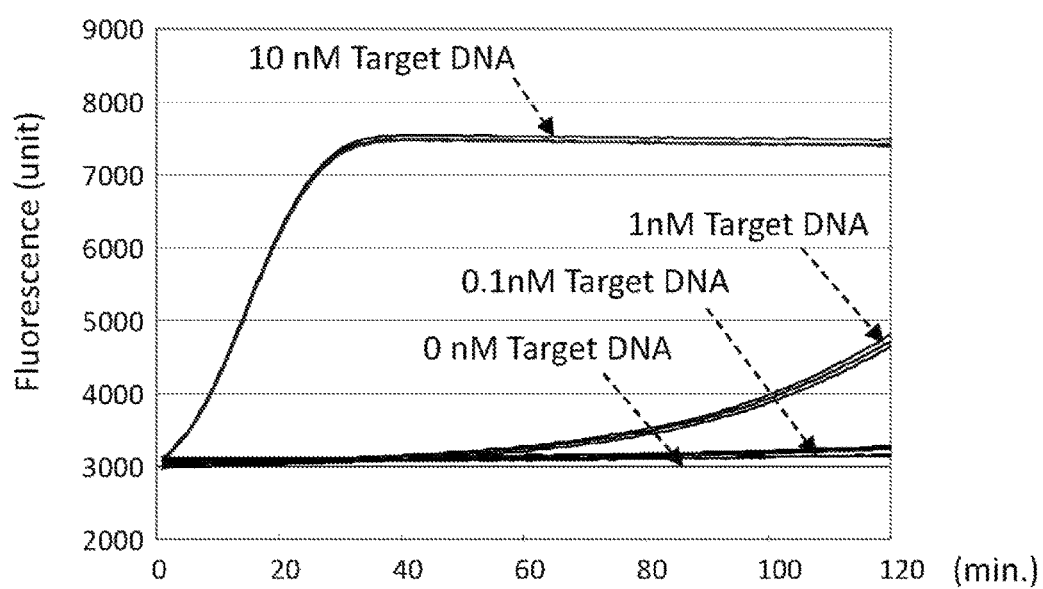
FIG. 5 depicts the results of reactions using CSC DNA #2 (SEQ ID NO.: 9) to detect different concentrations (10 nM, 1 nM, 0.1 nM, and 0.0 nM) of human micro RNA hsa-miR-24 target DNA (SEQ ID NO.: 6).

The results of the reactions using CSC DNA #2 to detect human micro RNA hsa-miR-24 target DNA (SEQ ID NO.: 6) at different concentrations (10 nM, 1 nM, 0.1 nM, and 0.0 nM) are shown in FIG. 5. In FIG. 5, the vertical axis shows the fluorescence intensity, and the horizontal axis shows time in minutes. Fluorescent measurements were performed at 37° C. at 1 minute intervals for 120 minutes using a Bio-Rad PCR system CFX 96.

Example 3

Reactions for detecting the presence of signal DNA in the presence and absence of target DNA were performed using the Covered Sequence Conversion DNA #3 represented by SEQ ID NO.: 11 (CSC DNA #3). The target nucleic acid was human micro RNA hsa-miR-24 (SEQ ID NO.:6).

The reactions were performed in a 25 µL reaction volume containing New England Biolabs (NEB) Buffer 2 having a final concentration of 10 mM Tris-HCl, 50 mM NaCl, 10 mM MgCl2, 1 mM DTT, pH 7.9. The nicking endonuclease used in the reaction was Nt.AlwI present at a concentration of 0.1 units/µL. The polymerase used in the reaction was Bst DNA Polymerase Large Fragment present at a concentration of 0.08 units/µL. The dNTP's were present at a final concentration 200 µM each. CSC DNA #3 was present in the reaction at a final concentration of 100 nM. A Molecular Beacon probe was used to detect the generation of signal DNA and was present at a final concentration of 100 nM.

CSC DNA #3 has the following sequence:

```
                                          (SEQ ID NO.: 11)
5'TGATAGCCCTGTACAATGCTGCTCAGAGATCCCAGGGC

TATCACTGTTCCTGCTGAACTGAGCCA3'-idT
```

CSC DNA #3 includes: an arbitrary sequence (A) (SEQ ID NO.: 2); a Nt.AlwI endonuclease recognition site (B) (SEQ ID NO.: 3) that can be used in a nicking reaction; a sequence (C) (SEQ ID NO.: 12) complementary to the arbitrary sequence (A) (SEQ ID NO.: 2); and a sequence (D) (SEQ ID NO.: 5) complementary to the target nucleic acid human micro RNA hsa-miR-24 (SEQ ID NO.: 6). CSC DNA #3 also has a 3'-end inverted thymidine modification.

To detect the presence of signal DNA generated after binding of the human micro RNA hsa-miR-24 target DNA (SEQ ID NO.: 6) to the CSC DNA #3, the following molecular beacon was used:

```
                                         (SEQ ID NO.: 8)
5' (FAM)-CGCGATGATAGCCCTGTACAATGCTGCTTCG

CG-(DABCYL) 3'
```

Figure 6:
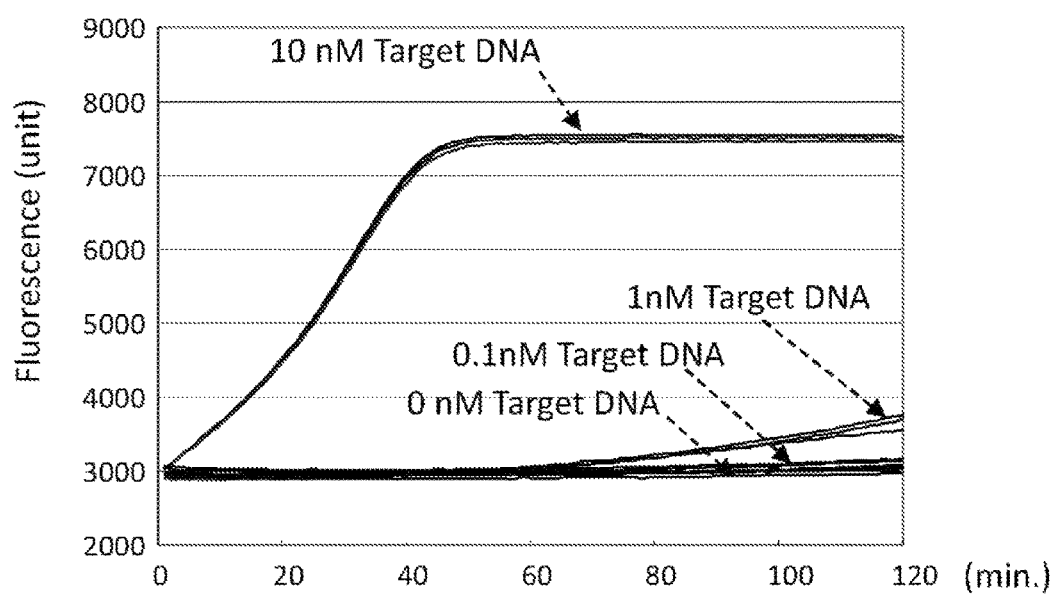
FIG. 6 depicts the results of reactions using CSC DNA #3 (SEQ ID NO.: 11) to detect different concentrations (10 nM, 1 nM, 0.1 nM, and 0.0 nM) of human micro RNA hsa-miR-24 target DNA (SEQ ID NO.: 6).

The results of reactions using CSC DNA #3 to detect target DNA at different concentrations (10 nM, 1 nM, 0.1 nM, and 0.0 nM) are shown in FIG. 6. In FIG. 6, the vertical axis shows the fluorescence intensity, and the horizontal axis shows time in minutes. Fluorescent measurements were performed at 37° C. at 1 minute intervals for 120 minutes using a Bio-Rad PCR system CFX 96.

Example 4

Reactions for detecting the presence of signal DNA in the presence and absence of target DNA were performed using the Covered Sequence Conversion DNA #4 represented by SEQ ID NO.: 13 (CSC DNA #4). The target nucleic acid was human micro RNA hsa-miR-24 (SEQ ID NO.:6).

The reactions were performed in a 25 µL reaction volume containing New England Biolabs (NEB) Buffer 2 having a final concentration of 10 mM Tris-HCl, 50 mM NaCl, 10 mM MgCl2, 1 mM DTT, pH 7.9. The nicking endonuclease used in the reaction was Nb.BbvCI, which was present at a concentration of 0.1 units/µL. The polymerase used in the reaction was Bst DNA Polymerase Large Fragment, which was present at a concentration of 0.08 units/µL. The dNTP's were present at a final concentration 200 µM each. CSC DNA #4 was present in the reaction at a final concentration of 100 nM. A Molecular Beacon probe present at a final concentration of 100 nM was used to detect the generation of signal DNA.

CSC DNA #4 has the following sequence:

```
                                          (SEQ ID NO.: 13)
5'TGATAGCCCTGTACAATGCCTCAGCCATTGTACAGGGC

TATCACTGTTCCTGCTGAACTGAGCCA3'-idT
```

CSC DNA #4 includes: an arbitrary sequence (A) (SEQ ID NO.: 14); a Nb.BbvCI endonuclease recognition site (B) (SEQ ID NO.: 15) that can be used in a nicking reaction; a sequence (C) (SEQ ID NO.: 16) complementary to the arbitrary sequence (A) (SEQ ID NO.: 14); and a sequence (D) (SEQ ID NO.: 5) complementary to the target nucleic acid human micro RNA hsa-miR-24 (SEQ ID NO.: 6). CSC DNA #4 also has a 3'-end inverted thymidine modification.

To detect the presence of signal DNA generated after binding of the human micro RNA hsa-miR-24 target DNA (SEQ ID NO.: 6) to the CSC DNA #4, the following molecular beacon was used:

```
                                         (SEQ ID NO.: 31)
5' (FAM)-CGATGATAGCCCTGTACAATGCCTCA

TCG-(DABCYL) 3'
```

Figure 7:
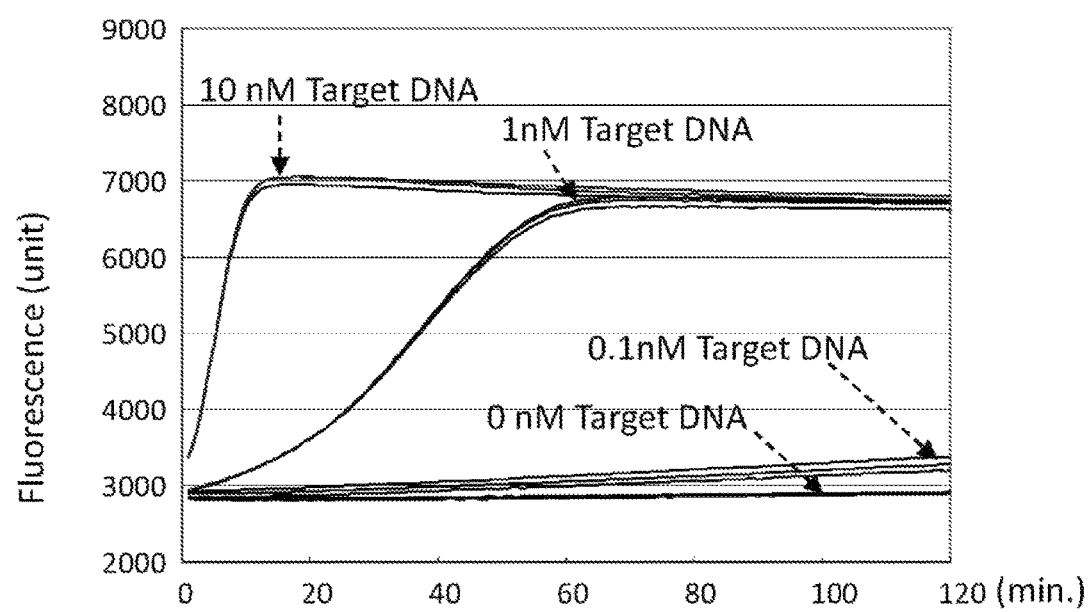
FIG. 7 depicts the results of reactions using CSC DNA #4 (SEQ ID NO.: 13) to detect different concentrations (10 nM, 1 nM, 0.1 nM, and 0.0 nM) of human micro RNA hsa-miR-24 target DNA (SEQ ID NO.: 6).

The results of reactions using CSC DNA #4 to detect human micro RNA hsa-miR-24 (SEQ ID NO.:6) target DNA at different concentrations (10 nM, 1 nM, 0.1 nM, and 0.0 nM) are shown in FIG. 7. In FIG. 7, the vertical axis shows the fluorescence intensity, and the horizontal axis shows time in minutes. Fluorescent measurements were performed at 37° C. at 1 minute intervals for 120 minutes using a Bio-Rad PCR system CFX 96.

Example 5

Reactions for detecting the presence of signal DNA in the presence and absence of target DNA were performed using Covered Sequence Conversion DNA #5 represented by SEQ ID NO.: 17 (CSC DNA #5). The target nucleic acid was human micro RNA hsa-miR-24 (SEQ ID NO.:6).

The reactions were performed in a 25 µL reaction volume containing New England Biolabs (NEB) Buffer 2 having a final concentration of 10 mM Tris-HCl, 50 mM NaCl, 10 mM MgCl2, 1 mM DTT, pH 7.9. The nicking endonuclease used in the reaction was Nb.BbvCI, which was present at a concentration of 0.1 units/µL. The polymerase used in the reaction was Bst DNA Polymerase Large Fragment, which was present at a concentration of 0.08 units/µL. The dNTP's were present at a final concentration 200 µM each. CSC DNA #5 was present in the reaction at a final concentration of 100 nM. A Molecular Beacon probe present at a final concentration of 100 nM was used to detect the generation of signal DNA.

CSC DNA #5 has the following sequence:

```
                                            (SEQ ID NO.: 17)
5'TGATAGCCCTGTACAATGCCTCAGCTTGTACAGGGCTA

TCACTGTTCCTGCTGAACTGAGCCA3'-idT
```

CSC DNA #5 includes: an arbitrary sequence (A) (SEQ ID NO.: 14); a Nb.BbvCI endonuclease recognition site (B) (SEQ ID NO.: 15) that can be used in a nicking reaction; a sequence (C) (SEQ ID NO.: 18) complementary to the arbitrary sequence (A) (SEQ ID NO.: 14); and a sequence (D) (SEQ ID NO.: 5) complementary to the target nucleic acid human micro RNA hsa-miR-24 (SEQ ID NO.: 6). CSC DNA #5 also has a 3'-end inverted thymidine modification.

To detect the presence of signal DNA generated after binding of the human micro RNA hsa-miR-24 target DNA (SEQ ID NO.: 6) to the CSC DNA #5, the following molecular beacon was used:

```
                                            (SEQ ID NO.: 31)
5' (FAM)-CGATGATAGCCCTGTACAATGCCTCA

TCG-(DABCYL) 3'
```

Figure 8:
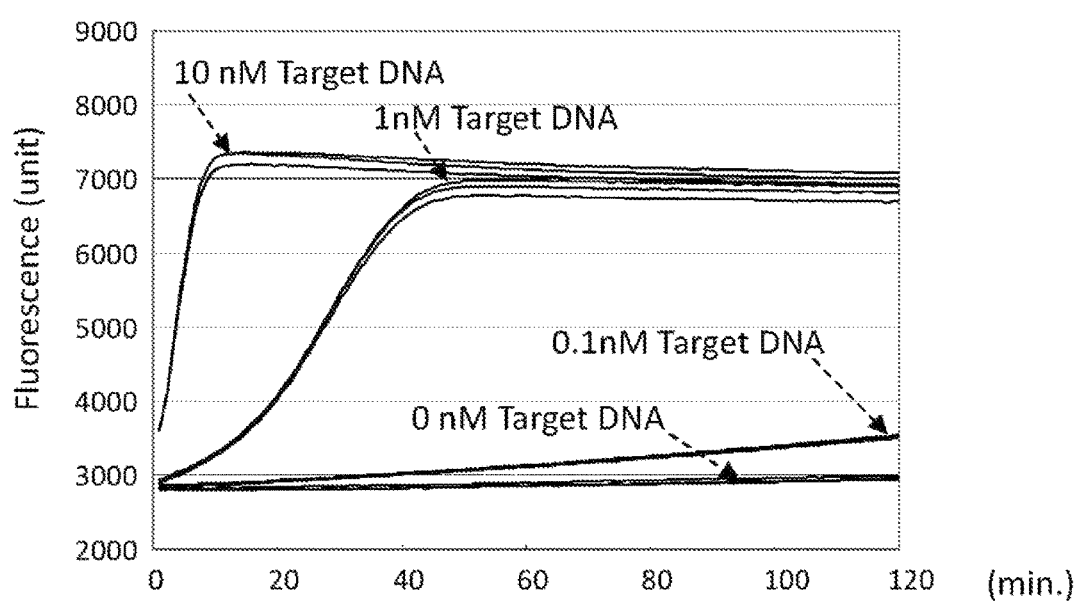
FIG. 8 depicts the results of reactions using CSC DNA #5 (SEQ ID NO.: 17) to detect different concentrations (10 nM, 1 nM, 0.1 nM, and 0.0 nM) of human micro RNA hsa-miR-24 target DNA (SEQ ID NO.: 6).

The results of the reactions using CSC DNA #5 to detect human micro RNA hsa-miR-24 (SEQ ID NO.:6) target DNA at different concentrations (10 nM, 1 nM, 0.1 nM, and 0.0 nM) are shown in FIG. 8. In FIG. 8, the vertical axis shows the fluorescence intensity, and the horizontal axis shows time in minutes. Fluorescent measurements were performed at 37° C. at 1 minute intervals for 120 minutes using a Bio-Rad PCR system CFX 96.

Example 6

Reactions for detecting the presence of signal DNA in the presence and absence of target DNA were performed using Covered Sequence Conversion DNA #6 represented by SEQ ID NO.: 19 (CSC DNA #6). The target nucleic acid was human micro RNA hsa-miR-24 (SEQ ID NO.:6).

The reactions were performed in a 25 μL reaction volume containing New England Biolabs (NEB) Buffer 2 having a final concentration of 10 mM Tris-HCl, 50 mM NaCl, 10 mM MgCl2, 1 mM DTT, pH 7.9. The nicking endonuclease used in the reaction was Nb.BbvCI, which was present at a concentration of 0.1 units/μL. The polymerase used in the reaction was Bst DNA Polymerase Large Fragment, which was present at a concentration of 0.08 units/μL. The dNTP's were present at a final concentration 200 μM each. CSC DNA #6 was present in the reaction at a final concentration of 100 nM. A Molecular Beacon probe present at a final concentration of 100 nM was used to detect the generation of signal DNA.

CSC DNA #6 has the following sequence:

```
                                            (SEQ ID NO.: 19)
5'TGATAGCCCTGTACAATGCCTCAGCTACAGGGCTATCA

CTGTTCCTGCTGAACTGAGCCA3'-idT
```

CSC DNA #6 (SEQ ID NO. 19) includes: an arbitrary sequence (A) (SEQ ID NO.: 14); a Nb.BbvCI endonuclease recognition site (B) (SEQ ID NO.: 15) that can be used in a nicking reaction; a sequence (C) (SEQ ID NO.: 20) complementary to the arbitrary sequence (A) (SEQ ID NO.: 14); and a sequence (D) (SEQ ID NO.: 5) complementary to the target nucleic acid human micro RNA hsa-miR-24 (SEQ ID NO.: 6). CSC DNA #6 also has a 3'-end inverted thymidine modification.

To detect the presence of signal DNA generated after binding of the human micro RNA hsa-miR-24 target DNA (SEQ ID NO.: 6) to the CSC DNA #6, the following molecular beacon was used:

```
                                            (SEQ ID NO.: 31)
5' (FAM)-CGATGATAGCCCTGTACAATGCCTCA

TCG-(DABCYL) 3'
```

Figure 9:
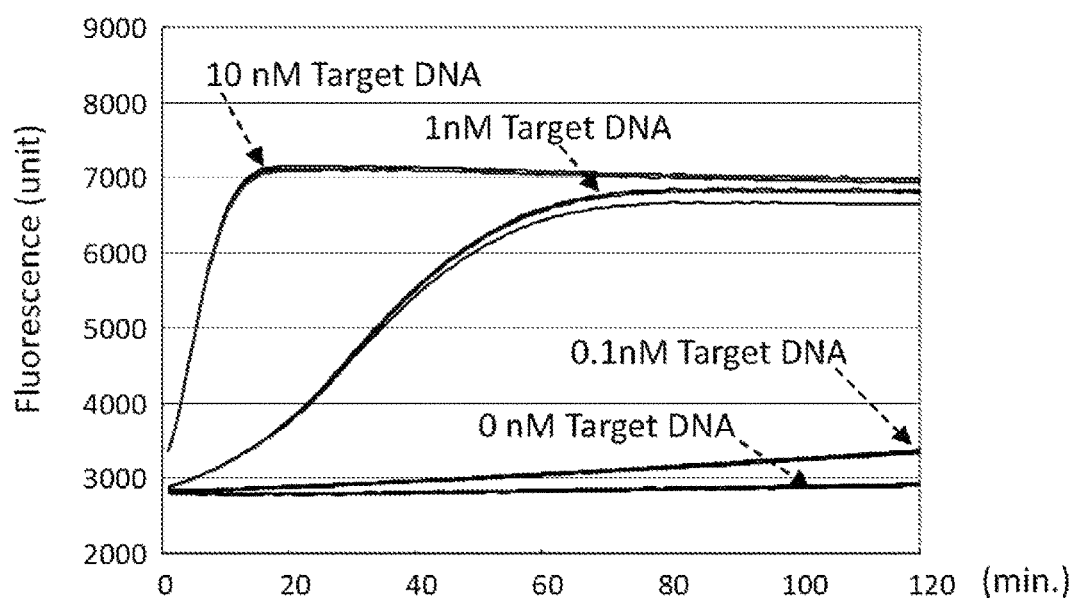
FIG. 9 depicts the results of reactions using CSC DNA #6 (SEQ ID NO.: 19) to detect different concentrations (10 nM, 1 nM, 0.1 nM, and 0.0 nM) of human micro RNA hsa-miR-24 target DNA (SEQ ID NO.: 6).

The results of the reactions using CSC DNA #6 to detect target DNA present at different concentrations (10 nM, 1 nM, 0.1 nM, and 0.0 nM) are shown in FIG. 9. In FIG. 9, the vertical axis shows the fluorescence intensity, and the horizontal axis shows time in minutes. Fluorescent measurements were performed at 37° C. at 1 minute intervals for 120 minutes using a Bio-Rad PCR system CFX 96.

Example 7

*Chlamydia* is a non-motile, Gram-negative, obligate intracellular parasite of eukaryotic cells. Methods according to the present invention can be used to test biological samples for the presence or absence of target nucleic acids originating from *Chlamydia*. For example, a CSC DNA as described herein can be used, wherein the sequence (D) complementary to a target nucleic acid comprises a sequence (D) that is complementary to a nucleic acid originating from *Chlamydia*.

Samples can be swab specimens taken from the endocervix, the vagina, urethra, or urine specimens from subjects. Sample preparation can be performed using Abbott's m2000sp sample preparation system, which fully automates the extraction of the nucleic acid from the specimen and then dispenses extracted nucleic acid into a 96-well optical reaction plate. In addition to the extracted nucleic acid, the following can also be dispensed into the 96-well plate: (1) CSC DNA having a sequence (D) that is complementary to a nucleic acid originating from *Chlamydia*; (2) a polymerase; and (3) an endonuclease for nicking the endonuclease site (B) of the CSC DNA. In addition, reaction buffers and other reagents (e.g., dNTPs and molecular beacon probes) can be dispensed into the 96-well plate as required.

Example 8

*Neisseria gonorrhoeae* is a species of Gram-negative coffee bean-shaped diplococci bacteria responsible for the sexually transmitted infection gonorrhea. Methods according to the present invention can be used to test biological samples for the presence or absence of target nucleic acids originating from *N. gonorrhoeae*. For example, a CSC DNA as described herein can be used, wherein the sequence (D) complementary to a target nucleic acid comprises a sequence (D) that is complementary to a nucleic acid originating from *N. gonorrhoeae*.

Samples can be swab specimens taken from the male urethra, the endocervix, or the vagina, or urine specimens from males and females. Sample preparation can be performed using Abbott's m2000sp sample preparation system, which fully automates the extraction of the nucleic acid from the specimen and then dispenses extracted nucleic acid into a 96-well optical reaction plate. In addition to the extracted nucleic acid, the following can also be dispensed into 96-well optical reaction plate: (1) CSC DNA having a sequence (D) that is complementary to a nucleic acid originating from N. gonorrhoeae; (2) a polymerase; and (3) an endonuclease for nicking the endonuclease site (B) of the CSC DNA. In addition, reaction buffers and other reagents (e.g., dNTPs and molecular beacon probes) can be dispensed into the 96-well plate as required.

Example 9

Hepatitis C (HCV) virus is a single-stranded RNA virus, with a genome of 9,500 nucleotides. Methods according to the present invention can be used to test biological samples for the presence or absence of target nucleic acids originating from HCV. For example, a CSC DNA as described herein can be used, wherein the sequence (D) complementary to a target nucleic acid comprises a sequence (D) that is complementary to a nucleic acid originating from HCV.

Human serum and plasma (EDTA) specimens can be used. Sample preparation can be performed using Abbott's m2000sp sample preparation system, which fully automates the extraction of the nucleic acid from the specimen and then dispenses extracted nucleic acid into a 96-well optical reaction plate. In addition to the extracted nucleic acid, the following can also be dispensed into the 96-well plate: (1) CSC DNA having a sequence (D) that is complementary to a nucleic acid originating from HCV; (2) a polymerase; and (3) an endonuclease for nicking the endonuclease site (B) of the CSC DNA. In addition, reaction buffers and other reagents (e.g., dNTPs and molecular beacon probes) can be dispensed into the 96-well plate as required.

Varied genotypes of HCV can also be detected using methods according to the present invention. For example, a CSC DNA described above can be used, wherein the sequence (D) complementary to a target nucleic acid is replaced with a sequence (D) that is complementary to a nucleic acid originating from HCV genotype II. Sample preparation can be performed as above described above.

Example 10

HBV is a small, circular, partially double stranded DNA virus of approximately 3,200 base pairs, and methods according to the present invention can be used to detect the presence or absence of a target HBV nucleic acid in a sample. For example, a CSC DNA as described herein can be used, wherein the sequence (D) complementary to a target nucleic acid comprises a sequence (D) that is complementary to a nucleic acid originating from HBV.

Human serum and plasma (EDTA) specimens can be used. Sample preparation can be performed using Abbott's m2000sp sample preparation system, which fully automates the extraction of the nucleic acid from the specimen and then dispenses extracted nucleic acid into a 96-well optical reaction plate. In addition to the extracted nucleic acid, the following can also be dispensed into the 96-well plate: (1) CSC DNA having a sequence (D) that is complementary to a nucleic acid originating from HBV; (2) a polymerase; and (3) an endonuclease for nicking the endonuclease site (B) of the CSC DNA. In addition, reaction buffers and other reagents (e.g., dNTPs and molecular beacon probes) can be dispensed into the 96-well plate as required.

Example 11

Human immunodeficiency virus-1 (HIV-1) is a retrovirus that causes acquired immunodeficiency syndrome (AIDS). Methods according to the present invention can be used to detect the presence of HIV-1 nucleic acid in a sample. For example, a CSC DNA as described herein can be used, wherein the sequence (D) complementary to a target nucleic acid comprises a sequence (D) that is complementary to a nucleic acid originating from HIV-1.

Sample preparation can be performed using Abbott's m2000sp sample preparation system, which fully automates the extraction of the nucleic acid from the specimen and then dispenses extracted nucleic acid into a 96-well optical reaction plate. In addition to the extracted nucleic acid, the following can also be dispensed into the 96-well plate: (1) CSC DNA having a sequence (D) that is complementary to a nucleic acid originating from HIV-1; (2) a polymerase; and (3) an endonuclease for nicking the endonuclease site (B) of the CSC DNA. In addition, reaction buffers and other reagents (e.g., dNTPs and molecular beacon probes) can be dispensed into the 96-well plate as required.

While the application has been described with reference to certain aspects and embodiments, it will be understood by those skilled in the art that changes may be made to the disclosure provided herein, and equivalents may be substituted without departing from the scope of the disclosure. Accordingly, the application should not be limited to the particular aspects and embodiments disclosed, but should be understood and appreciated to include all aspect and embodiments falling within the scope of the appended claims.

TABLE 1

| Conversion DNA | Stem/Loop | Signal* at 120 minutes using 10 nM Target (Signal/Target Ratio) | Signal* at 120 minutes using 1 nM Target (Signal/Target Ratio) | Signal* at 120 minutes using 0.1 nM Target (Signal/Target Ratio) |
| --- | --- | --- | --- | --- |
| USC DNA #1 (SEQ ID NO.: 7) | NA | 10.0 | 6.6 | 5.7 |
| CSC DNA #1 (SEQ ID NO.: 1) | Stem 18/ Loop 13 | 10.0 | 43.7 | 48.4 |
| CSC DNA #2 (SEQ ID NO.: 9) | Stem 21/ Loop 10 | 10.0 | 38.0 | 47.4 |
| CSC DNA #3 (SEQ ID NO.: 11) | Stem 11/ Loop 21 | 10.0 | 15.6 | 36.3 |
| CSC DNA #4 (SEQ ID NO.: 13) | Stem 18/ Loop 7 | 10.0 | 98.4 | 116.4 |
| CSC DNA #5 (SEQ ID NO.: 17) | Stem 16/ Loop 9 | 10.0 | 95.3 | 169.9 |

TABLE 1-continued

| Conversion DNA | Stem/Loop | Signal* at 120 minutes using 10 nM Target (Signal/Target Ratio) | Signal* at 120 minutes using 1 nM Target (Signal/Target Ratio) | Signal* at 120 minutes using 0.1 nM Target (Signal/Target Ratio) |
|---|---|---|---|---|
| CSC DNA #6 (SEQ ID NO.: 19) | Stem 13/ Loop 12 | 10.0 | 95.0 | 130.6 |

*Fluorescent signal above background. Background is defined as the signal at 0 nM target nucleic acid.

The invention claimed is:

1. A method for detecting a target nucleic acid in a sample, said method comprising
contacting said sample with:
a hairpin oligonucleotide comprising, in the 5' to 3' direction, a first arbitrary sequence, an endonuclease recognition site, a sequence complementary to said first arbitrary sequence, a sequence complementary to the 3' end of a target nucleic acid, and a 3'-end modification;
a polymerase; and
an endonuclease for a nicking reactions;
to form a reaction mixture;
maintaining the reaction mixture under conditions that
allow the target nucleic acid to bind to said hairpin oligonucleotide at said sequence complementary to the 3' end of the target nucleic acid, wherein upon binding, the 3' end of the target nucleic acid initiates strand displacement replication to produce an extended target nucleic acid sequence comprising the complementary sequence to the endonuclease recognition site and the first arbitrary sequence; and
allow the endonuclease to produce a nick in the extended target nucleic acid, which primes further strand displacement replication to produce a signal DNA comprising sequence complementary to the first arbitrary sequence; and
detecting the signal DNA, wherein the presence of the signal DNA detects the target nucleic acid.

2. The method of claim 1 wherein said method is performed at a constant temperature.

3. The method of claim 1 wherein said method is performed at a temperature of from about 20° C. to about 42° C.

4. The method of claim 1 wherein said method is performed at a temperature of about 37° C.

5. The method of claim 1 wherein said target is a micro-RNA.

6. The method of claim 1 wherein said target is a micro-RNA selected from the group consisting of hsa-miR-24, hsa-miR-107, hsa-miR-221, hsa-miR-21, hsa-miR-500 and hsa-miR-106a.

7. The method of claim 1 wherein said target originates from an infectious agent.

8. The method of claim 1 wherein said target nucleic acid originates from an infectious agent selected from the group consisting of hepatitis B virus, hepatitis C virus, human immunodeficiency virus, *Chlamydia trachomatis, Neisseria gonorrhoeae*, influenza A virus, influenza B virus, or respiratory syncytial virus.

9. The method of claim 1 wherein said target nucleic acid comprises a sequence within any of SEQ ID NO: 6, SEQ ID NO: 21, SEQ ID NO: 22, SEQ ID NO: 23, SEQ ID NO: 24, SEQ ID NO.: 25, SEQ ID NO: 26, SEQ ID NO: 27, SEQ ID NO: 28, SEQ ID NO: 29, or SEQ ID NO: 30.

10. The method of claim 1 wherein the oligonucleotide further comprises a modification at the 5' end, at the endonuclease recognition site, or at both the 5' end and the endonuclease recognition site.

* * * * *

UNITED STATES PATENT AND TRADEMARK OFFICE
CERTIFICATE OF CORRECTION

PATENT NO. : 10,036,077 B2
APPLICATION NO. : 14/597981
DATED : July 31, 2018
INVENTOR(S) : Ken Komiya, Makoto Komori and Toru Yoshimura It is certified that error appears in the above-identified patent and that said Letters Patent is hereby corrected as shown below:

On the Title Page

Please delete:
Item "(71) Applicants: ABBOTT JAPAN CO., LTD., Chiba (JP);
TOKYO INSTITUTE OF TECHNOLOGY, Tokyo (JP)"

Please insert:
Item --(71) Applicants: ABBOTT LABORATORIES, Abbott Park, IL (US);
TOKYO INSTITUTE OF TECHNOLOGY, Tokyo (JP)--

Signed and Sealed this
Thirtieth Day of April, 2019

Andrei Iancu
*Director of the United States Patent and Trademark Office*